US012558158B2

(12) United States Patent　　　　(10) Patent No.:　US 12,558,158 B2
Hancock et al.　　　　　　　　　　(45) Date of Patent:　Feb. 24, 2026

(54) ELECTROSURGICAL INSTRUMENT WITH NON-LIQUID THERMAL TRANSFER

(71) Applicant: Creo Medical Limited, Chepstow (GB)

(72) Inventors: Christopher Paul Hancock, Chepstow (GB); Patrick Burn, Chepstow (GB)

(73) Assignee: Creo Medical Limited, Chepstow (GB)

( * ) Notice: Subject to any disclaimer, the term of this patent is extended or adjusted under 35 U.S.C. 154(b) by 942 days.

(21) Appl. No.: 17/607,646

(22) PCT Filed: Apr. 3, 2020

(86) PCT No.: PCT/EP2020/059625

§ 371 (c)(1),
(2) Date: Oct. 29, 2021

(87) PCT Pub. No.: WO2020/221552

PCT Pub. Date: Nov. 5, 2020

(65) Prior Publication Data

US 2022/0211435 A1　　Jul. 7, 2022

(30) Foreign Application Priority Data

Apr. 30, 2019　(GB) ...................................... 1906011

(51) Int. Cl.
　　*A61B 18/14*　　　(2006.01)
　　*A61B 18/18*　　　(2006.01)
　　*A61B 18/00*　　　(2006.01)
(52) U.S. Cl.
　　CPC .............................. *A61B 18/1815* (2013.01);
　　　　　　　*A61B 2018/00005* (2013.01); *A61B 2018/00101* (2013.01);
(Continued)
(58) Field of Classification Search
　　CPC .................. A16B 18/1815; A61B 2018/00005
　　See application file for complete search history.

(56) References Cited

U.S. PATENT DOCUMENTS 5,861,021 A　　　1/1999　Thome et al.
6,480,746 B1 *　11/2002　Ingle ................... A61B 18/1485
　　　　　　　　　　　　　　　606/41
(Continued)

FOREIGN PATENT DOCUMENTS

CN　　　104 519 940 A　　4/2015
EP　　　　1055400 A1　　11/2000
(Continued)

OTHER PUBLICATIONS

Search Report dated Oct. 22, 2019 in connection with GB Application No. 1906011.0.
(Continued)

*Primary Examiner* — Linda C Dvorak
*Assistant Examiner* — Ryan T Clark
(74) *Attorney, Agent, or Firm* — Wolf, Greenfield & Sacks, P.C.

(57)　　　　　　ABSTRACT

Various embodiments provide an electrosurgical instrument comprising: a flexible coaxial transmission line arranged to convey microwave energy; a radiating tip portion connected at a distal end of the flexible coaxial transmission line and configured to receive the microwave energy, the radiating tip portion comprising: a distal coaxial transmission line for conveying the microwave energy; and a needle tip mounted at a distal end of the distal coaxial transmission line, the needle tip being arranged to deliver the microwave energy into biological tissue; and a heat sink mounted at an interface between the flexible coaxial transmission line and radiating tip portion. The heat sink is in thermal communication with a proximal end of the distal coaxial transmission line and configured to draw thermal energy from the radiating tip portion. Also, a maximum outer diameter of the radiating tip portion is smaller than an outer diameter of the flexible
(Continued)

coaxial transmission line. An associated electrosurgical system is also disclosed.

18 Claims, 3 Drawing Sheets

(52) U.S. Cl.
CPC ............... *A61B 2018/00577* (2013.01); *A61B 2018/00916* (2013.01); *A61B 2018/00982* (2013.01); *A61B 2018/1869* (2013.01)

(56) References Cited

U.S. PATENT DOCUMENTS

| | | | |
|---|---|---|---|
| 6,533,780 B1 * | 3/2003 | Laird ................. | A61B 18/1485 |
| | | | 606/41 |
| 2001/0039416 A1 * | 11/2001 | Moorman .......... | A61B 10/0275 |
| | | | 607/101 |
| 2005/0245920 A1 | 11/2005 | Vitullo et al. | |
| 2008/0082093 A1 | 4/2008 | Prakash et al. | |
| 2008/0266203 A1 | 10/2008 | Rossetto et al. | |
| 2011/0077632 A1 | 3/2011 | Rossetto | |
| 2011/0319880 A1 | 12/2011 | Prakash et al. | |
| 2014/0046316 A1 * | 2/2014 | Ladtkow ................ | A61B 1/018 |
| | | | 606/33 |
| 2014/0296839 A1 * | 10/2014 | Brannan ............ | A61B 18/1815 |
| | | | 606/33 |
| 2018/0036081 A1 | 2/2018 | Dickhans et al. | |
| 2019/0069951 A1 | 3/2019 | Hancock et al. | |
| 2019/0117306 A1 | 4/2019 | Hancock et al. | |

FOREIGN PATENT DOCUMENTS

| | | | |
|---|---|---|---|
| EP | 1767165 | A1 | 3/2007 |
| JP | 2008-086774 | A | 4/2008 |
| JP | 2013-176628 | A | 9/2013 |
| WO | WO 2018/220177 | A1 | 12/2018 |

OTHER PUBLICATIONS

International Search Report and Written Opinion mailed May 28, 2020 in connection with International Application No. PCT/EP2020/059625.
Japanese Office Action mailed Nov. 21, 2023, in connection with Japanese Application No. 2021-564205.
Chinese Office Action dated Nov. 24, 2023, in connection with Chinese Application No. 202080032545.4.
GB 1906011.0, Oct. 22, 2019, Search Report.
PCT/EP2020/059625, May 28, 2020, International Search Report and Written Opinion.

* cited by examiner

ELECTROSURGICAL INSTRUMENT WITH NON-LIQUID THERMAL TRANSFER

CROSS REFERENCE TO RELATED APPLICATION

This Application is a national stage filing under 35 U.S.C. 371 of International Patent Application Serial No. PCT/EP2020/059625, filed Apr. 3, 2020, entitled "ELECTRO-SURGICAL INSTRUMENT WITH NON-LIQUID THERMAL TRANSFER". Foreign priority benefits are claimed under 35 U.S.C. § 119(a)-(d) or 35 U.S.C. § 365(b) of British application number 1906011.0, filed Apr. 30, 2019. The entire contents of these applications are incorporated herein by reference in their entirety.

FIELD OF THE INVENTION

The invention relates to an electrosurgical instrument for delivering electromagnetic energy to biological tissue in order to ablate or coagulate target tissue. The electrosurgical instrument may be part of an electrosurgical system that includes an electrosurgical generator for supplying RF and/or microwave energy, where the electrosurgical instrument is arranged to receive the microwave and/or RF energy and deliver it to target tissue. The electrosurgical instrument may be arranged to ablate or coagulate or ablate and coagulate tissue, such as a tumour, cyst or other lesion. In the instance of coagulation, the microwave energy may be used to create a plug to cut off the supply of blood to a tumour; it may be desirable to also ablate the tumour mass once the supply has been cut off. The electrosurgical instrument may be particularly suited for treatment of tissue in the pancreas, the lung, the kidney, brain or the liver.

BACKGROUND TO THE INVENTION

Electromagnetic (EM) energy, and in particular microwave and radiofrequency (RF) energy, has been found to be useful in electrosurgical operations, for its ability to cut, coagulate, and ablate body tissue. Typically, apparatus for delivering EM energy to body tissue includes a generator comprising a source of EM energy, and an electrosurgical instrument connected to the generator, for delivering the energy to tissue. Conventional electrosurgical instruments are often designed to be inserted percutaneously into the patient's body. However, it can be difficult to locate the instrument percutaneously in the body, for example if the target site is in a moving lung or a thin walled section of the gastrointestinal (GI) tract. Other electrosurgical instruments can be delivered to a target site by a surgical scoping device (e.g. an endoscope) which can be run through channels in the body such as airways or the lumen of the oesophagus or colon. This allows for minimally invasive treatments, which can reduce the mortality rate of patients and reduce intra-operative and postoperative complication rates.

Tissue ablation using microwave EM energy is based on the fact that biological tissue is largely composed of water. Human soft organ tissue is typically between 70% and 80% water content. Water molecules have a permanent electric dipole moment, meaning that a charge imbalance exists across the molecule. This charge imbalance causes the molecules to move in response to the forces generated by application of a time varying electric field as the molecules rotate to align their electric dipole moment with the polarity of the applied field. At microwave frequencies, rapid molecular oscillations result in frictional heating and consequential dissipation of the field energy in the form of heat. This is known as dielectric heating. Water (a major component of blood) has a much higher dipole moment than fatty tissue and so for the same electric field, the heating of the water molecules in blood will occur more rapidly than the heating of the fat molecule.

This principle is harnessed in microwave ablation therapies, where water molecules in target tissue are rapidly heated by application of a localised electromagnetic field at microwave frequencies, resulting in tissue coagulation and cell death. It is known to use microwave emitting probes to treat various conditions in the lungs and other organs. For example, in the lungs, microwave radiation can be used to treat asthma and ablate tumours or lesions.

One challenge facing the delivery of microwave energy to treatment sites located within the body is how to prevent unwanted effects caused by losses from the cable that conveys the microwave energy to the treatment site. These losses often manifest as heating of the cable, which in turn can heat and potentially damage biological tissue.

Such heating effects can be ameliorated by cooling the cable. Typically this is done by circulating a liquid coolant. However, the space required for coolant circulation within a cable presents a barrier to further miniaturisation of the cable itself, and any distal probe that may also require cooling. On the other hand, it is desirable for cables and probes to be as small as possible in order to gain access to treatment sites in the finer parts of the bronchial tree structure of the lungs, for example.

SUMMARY OF THE INVENTION

At its most general, the invention provides an electrosurgical instrument having a non-liquid thermal energy transfer mechanism that operates to draw heat away from the distal end thereof. The thermal energy transfer mechanism may provide a thermal gradient for the instrument that provides a preferential route for the transfer of thermal energy. The thermal gradient may be provided by a heat sink (or thermal mass) disposed at a distal end of a coaxial cable that conveys microwave energy. The heat sink may be made from a material having a higher thermal conductivity that a distal instrument tip. The heat sink may be actively cooled by providing a thermally conductive connection to a cooling device or coolant source located at a proximal end of the cable (i.e. remote from the treatment site).

In one aspect, the invention provides an electrosurgical instrument comprising: a flexible coaxial transmission line arranged to convey microwave energy; a radiating tip portion connected at a distal end of the flexible coaxial transmission line and configured to receive the microwave energy, the radiating tip portion comprising: a distal coaxial transmission line for conveying the microwave energy; and a needle tip mounted at a distal end of the distal coaxial transmission line, the needle tip being arranged to deliver the microwave energy into biological tissue; and a heat sink mounted at an interface between the flexible coaxial transmission line and radiating tip portion, wherein the heat sink is in thermal communication with a proximal end of the distal coaxial transmission line and configured to draw thermal energy from the radiating tip portion, and wherein a maximum outer diameter of the radiating tip portion is smaller than an outer diameter of the flexible coaxial transmission line. The heat sink thus operates to draw thermal energy in the radiating tip portion (i.e. heat generated by losses in the distal coaxial transmission line) in a proximal direction away from radiating tip portion. This technique may prevent a concentration of thermal loss from occurring around the radiating tip, which avoids unwanted damage to surrounding tissue, without adversely affecting the delivered microwave energy.

The heat sink may be a solid body. Thus, in contrast to known fluid-based cooling systems, the instrument does not require space within the flexible shaft for delivery and extraction of fluid. This allows the cooling effect to be achieved for much smaller diameter devices.

The solid body may be disposed between an outer conductor of the distal coaxial transmission line and an outer conductor of the flexible coaxial transmission line. There is preferably a physical connection between the outer conductors and the heat sink, whereby the heat sink forms part of a continuous thermal transmission path away from the radiating tip portion.

The heat sink may be an annular body mounted around the proximal end of the distal coaxial transmission line. The heat sink may be formed from a material with high thermal conductivity, e.g. a metal such as copper or silver.

The instrument may further comprise a thermal isolator cap mounted over the interface between the flexible coaxial transmission line and radiating tip portion. The thermal isolator may be provided to isolate the heat sink from the surrounding biological tissue. This may further assist in defining the preferential path for heat flow away from the radiating portion, by inhibiting heat flow out of the distal end of the flexible shaft. The thermal isolator cap may also be useful in situations where the heat sink is actively cooled via the thermal transmission element (discussed in more detail below). In these examples, the thermal isolator cap may inhibit the cooling effect of the heat sink from adversely affecting the ablation effect of the field emitting by the antenna, and also may prevent the cooling effect from damaging surrounding tissue.

The thermal isolator cap may be formed from epoxy resin, or another suitable thermal insulator that can be moulded over the distal end of the flexible shaft.

The radiating tip portion may have a maximum outer diameter that is 1.0 mm or less. For example, the radiating tip portion may be 19 gauge. In some examples, the maximum outer diameter may be 0.95 mm, 0.9 mm or less. The maximum outer diameter may refer to the largest outer diameter of the radiating tip portion along a length of the radiating tip portion. The instrument may thus be able to access regions deeper in the lungs than conventional ablation devices.

The distal coaxial transmission line may be a half wavelength transformer to facilitate transfer of microwave energy to the antenna. An advantage of configuring the distal needle tip as a half wavelength transformer may be to minimise reflections at the interface between components, e.g. between the coaxial transmission line and distal coaxial transmission line, and between the distal coaxial transmission line and the needle tip. A reflection coefficient at the latter interface is typically larger due to a larger variation in impedance. The half wavelength configuration may minimise these reflections so that the dominant reflection coefficient becomes that of the interface between the distal coaxial transmission line and the tissue. The impedance of the distal coaxial transmission line may be selected to be identical or close to the expected tissue impedance to provides a good match at the frequency of the microwave energy. The radiating tip portion may have a length equal to or greater than 30 mm, e.g. 40 mm. In this manner, the radiating tip portion may be long enough for the distal needle tip to reach a treatment site, without having to insert a portion of the coaxial transmission line into tissue. In some cases the radiating tip portion may have a length of 140 mm or greater.

The instrument may further comprise a thermal transfer element disposed along the flexible coaxial transmission line, wherein the thermal transfer element provides a thermal gradient that draws heat energy from the radiating tip portion. The thermal transfer element if preferably actively cooled (e.g. exposed to a coolant source, or force cooled by a refrigerator or thermoelectric cooling effect) at a proximal end thereof, e.g. at a proximal end of the instrument. In one example, the thermal transfer element may be a sleeve of thermally conductive material mounted around an outer conductor of the flexible coaxial transmission line. The sleeve may be braided, e.g. made from a metal such as copper or gold. In one example, the thermal transfer element may be an outer conductor of the flexible coaxial transmission line. In other examples, the thermal transfer element is separate from the outer conductor, and may be separated therefrom by a thermal insulating layer, e.g. a layer of PTFE or other suitably flexible thermal insulator. In another example, the thermal transfer element may be made from yttrium-barium-copper-oxide or similar compound, which the inventors have found to be very effective at transferring by conduction a cooling effect of a proximal coolant source such as liquid nitrogen or liquid helium to a distal end of an instrument.

A distal portion of the thermal transfer element may be in thermal communication with the heat sink to draw thermal energy in a proximal direction along the flexible coaxial transmission line. In other words, the thermal transfer element actively cools the heat sink at the interface between the flexible coaxial transmission line and the distal coaxial transmission line. This may act to maintain the preferential flow path of heat energy away from the radiating tip portion through the instrument (rather than surrounding tissue) in a proximal direction.

The thermal transfer element comprises a solid body. In other words, it is distinct from fluid-based coolant circulation systems in conventional devices, and hence does not require the same volume within the instrument.

In another aspect, the invention provides an electrosurgical system comprising: an electrosurgical generator configured to generate microwave energy for ablating biological tissue; an electrosurgical instrument having a thermal transfer element as discussed above, wherein the instrument is connected to receive the microwave energy from the electrosurgical generator; and a cooling device arranged to force cool a proximal portion of the thermal transfer element the electrosurgical instrument. Any suitable means by the used to cool the thermal transfer element. The cooling device may be a thermoelectric cooler, for example. In other examples, the thermal transfer element may be kept cool by being brought into thermal contact with a cold body, e.g. a source of liquid nitrogen, liquid helium or the like. For example, the thermal transfer element may be dipped into or sprayed with liquid nitrogen or liquid helium. In such examples, it may be not be necessary to force cool the thermal transfer element; cooling may occur as the system attempts to find thermal equilibrium. In such examples, a temperature of a proximal end of the thermal transfer element may be less than −50° C., e.g. −100° C. or less.

The system may further comprise a surgical scoping device having a flexible insertion cord for insertion into a patient's body, the flexible insertion cord having an instrument channel running along its length, and wherein the electrosurgical instrument is dimensioned to be received within the instrument channel. The instrument may be usable with smaller diameter instrument channels than conventional instruments because the shaft that is inserted into the instrument channel does not need to contain a fluid-based coolant circulation system.

The system may further comprise a handpiece having a housing for receiving a proximal end of the electrosurgical instrument. The handpiece may comprise a control mechanism arranged to move the electrosurgical instrument relative to the housing to deploy a distal end of the electrosurgical instrument at a distal end of the instrument channel. The handpiece may be adapted to combine the control mechanism, a feed cable for providing microwave energy from the electrosurgical generator, and an input from the cooling device within the housing, whereby the flexible coaxial transmission line and thermal transfer element are combined in a single flexible shaft that is insertable into and slidable relative to the instrument channel of the scoping device.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate instrument. In use, the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Preferred spot frequencies for microwave EM energy include: 915 MHz, 2.45 GHz, 3.3 GHz, 5.8 GHz, 10 GHz, 14.5 GHz and 24 GHz. 5.8 GHz may be preferred. The device may deliver energy at more than one of these microwave frequencies.

The term "radiofrequency" or "RF" may be used to indicate a frequency between 300 kHz and 400 MHz.

BRIEF DESCRIPTION OF THE DRAWINGS

Embodiments of the invention are discussed below with reference to the accompanying drawings, in which.

DETAILED DESCRIPTION; FURTHER OPTIONS AND PREFERENCES

Figures 1, 2:
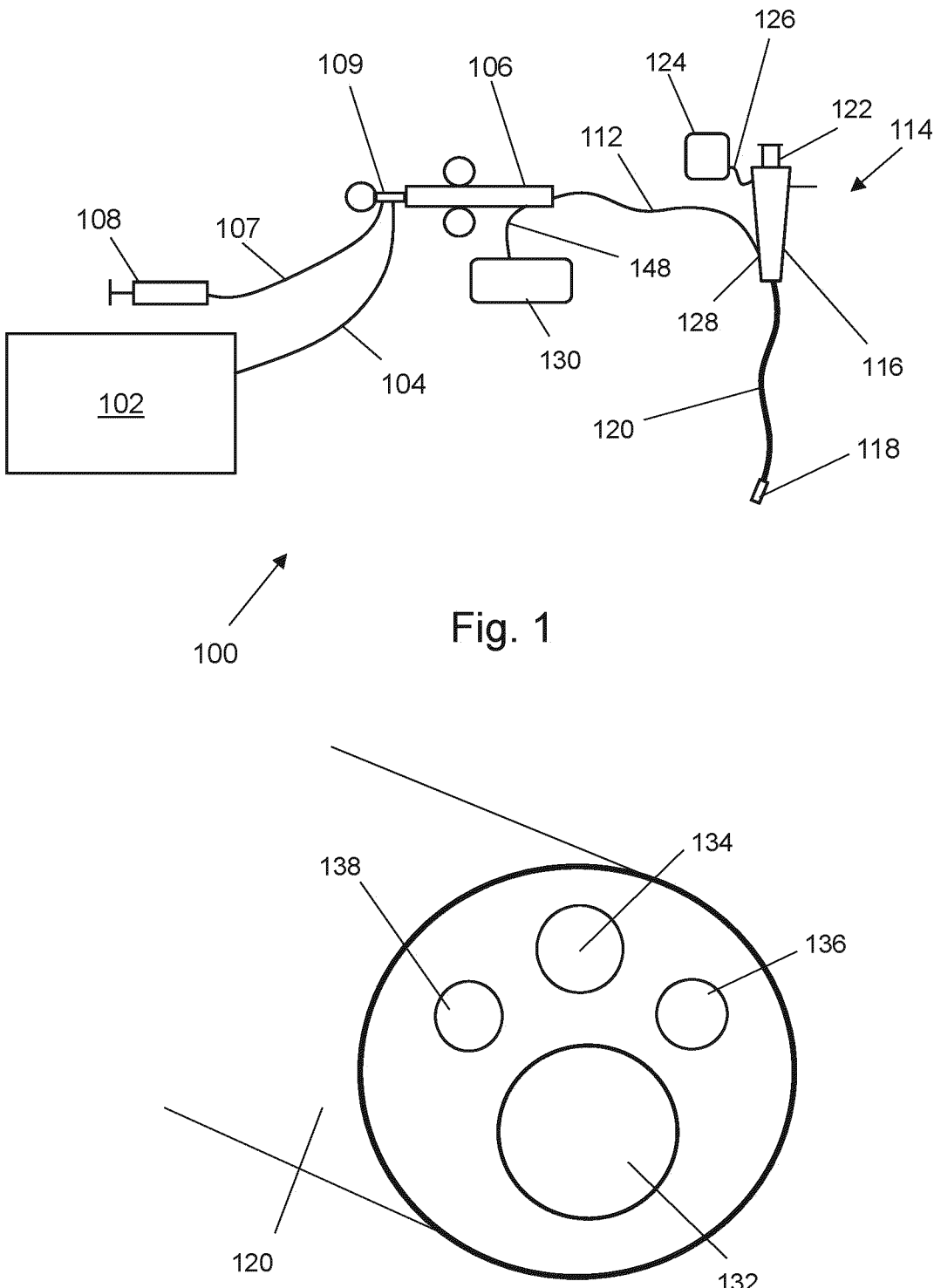
FIG. 1 is a schematic diagram of an electrosurgical system for tissue ablation that is an embodiment of the invention.
FIG. 2 is a schematic sectional view through an instrument cord of an endoscope that can be used with the present invention.

FIG. 1 is a schematic diagram of an electrosurgical system 100 that is an embodiment of the invention. The electrosurgical system 100 is capable of supplying microwave energy to a distal end of an invasive electrosurgical instrument to perform tissue ablation. The electrosurgical system is also capable of supplying a fluid, e.g. a liquid medicament or a cooling fluid, to a distal end of the invasive electrosurgical instrument. The system 100 comprises an electrosurgical generator 102 for controllably supplying microwave energy. The electrosurgical generator may be configured to supply pulsed microwave energy. A suitable generator for this purpose is described in WO 2012/076844, which is incorporated herein by reference. The electrosurgical generator 102 may be arranged to monitor reflected signals received back from the instrument in order to determine an appropriate power level for delivery. For example, the generator 102 may be arranged to calculate an impedance seen at the distal end of the instrument in order to determine an optimal delivery power level.

The electrosurgical system 100 further includes an interface joint 106 that is connected to the electrosurgical generator 102 via an interface cable 104. The interface joint 106 may also be connected via a fluid flow line 107 to a fluid delivery device 108, such as a syringe, although this is not essential. In some examples, the system may be arranged, additionally or alternatively, to aspirate fluid from a treatment site. In this scenario, the fluid flow line 107 may convey fluid away from the interface joint 106 to a suitable collector (not shown). The aspiration mechanism may be connected at a proximal end of the fluid flow line 107.

The interface joint 106 may house an instrument control mechanism 109 for controlling a position of the electrosurgical instrument. The control mechanism may be used to control a longitudinal position of the electrosurgical instrument, and/or bending of a distal end of the electrosurgical instrument. The control mechanism is operable by sliding a trigger, to control a longitudinal (back and forth) movement of one or more control wires or push rods (not shown). If there is a plurality of control wires, there may be multiple sliding triggers on the interface joint to provide full control.

In this example, the electrosurgical system 100 further includes an active cooling device 130 that is configured to cool a flexible elongate thermal transfer element 148, as discussed in more detail below. The active cooling device 130 may be any device suitable for providing a thermal cooling effect. For example it may be a refrigerator, or it may operate using thermoelectric cooling, e.g. a Peltier cooler or the like. In other examples, the cooling device 130 may be a cool body, e.g. of liquid nitrogen or liquid helium into which the thermal transfer element 148 is brought into contact, whereby the cooling 'effect' of the cool body is transferred by conduction along the length of the thermal transfer element 148 as it tries to reach thermal equilibrium.

A function of the interface joint 106 is to combine the inputs from the generator 102, fluid delivery device 108, cooling device 130 and instrument control mechanism into a single flexible shaft 112 (which may be part of the electrosurgical instrument discussed herein), which extends from the distal end of the interface joint 106.

The electrosurgical system 100 further includes a surgical scoping device 114, which in this example comprises an endoscopic ultrasound device, although it is to be understood that the invention may be used with any type of surgical scoping device 114 or flexible catheter (i.e. insertion tube without scoping functionality).

The flexible shaft 112 is insertable through an entire length of an instrument (working) channel of the surgical scoping device 114.

The surgical scoping device 114 comprises a body 116 having a number of input ports and an output port from which an instrument cord 120 extends. The instrument cord 120, which is illustrated in more detail in FIG. 2, comprises an outer jacket which surrounds a plurality of lumens. The plurality of lumens convey various things from the body 116 to a distal end of the instrument cord 120. One of the plurality of lumens is the instrument channel discussed above. Other lumens may include a channel for conveying optical radiation, e.g. to provide illumination at the distal end or to gather images from the distal end. The body 116 may include an eye piece 122 for viewing the distal end.

An endoscopic ultrasound device typically provides an ultrasound transducer on a distal tip of the instrument cord, beyond an exit aperture of the instrument channel. Signals from the ultrasound transducer may be conveyed by a suitable cable 126 back along the instrument cord to a processor 124, which can generate images in a known manner. The instrument channel may be shaped within the instrument cord to direct an instrument exiting the instrument channel through the field of view of the ultrasound system, to provide information about the location of the instrument at the target site.

The flexible shaft 112 has a distal assembly 118 (not drawn to scale in FIG. 1) that is shaped to pass through the instrument channel of the surgical scoping device 114 and protrude (e.g. inside the patient) at the distal end of the instrument cord. The distal assembly 118 may also be referred to herein as a radiating tip portion.

The structure of the distal assembly 118 discussed below may be particularly designed for use with an endoscopic ultrasound (EUS) device. The maximum outer diameter of the distal assembly 118 is equal to or less than 1.0 mm, e.g. less than 0.95 mm or 0.90 mm. The length of the flexible shaft can be equal to or greater than 1.2 m.

The body 116 includes an input port 128 for connecting to the flexible shaft 112. As explained below, a proximal portion of the flexible shaft may comprise a conventional coaxial cable capable of conveying the pulsed microwave energy from the electrosurgical generator 102 to the distal assembly 118. Example coaxial cables that are physically capable of fitting down the instrument channel of an EUS device are available with the following outer diameters: 1.19 mm (0.047"), 1.35 mm (0.053"), 1.40 mm (0.055"), 1.60 mm (0.063"), 1.78 mm (0.070"). Custom-sized coaxial cables (i.e. made to order) may also be used.

In order to control a position of a distal end of the instrument cord 120, the body 116 may further include a control actuator that is mechanically coupled to the distal end of the instrument cord 120 by one or more control wires (not shown), which extend through the instrument cord 120. The control wires may travel within the instrument channel or within their own dedicated channels. The control actuator may be a lever or rotatable knob, or any other known catheter manipulation device. The manipulation of the instrument cord 120 may be software-assisted, e.g. using a virtual three-dimensional map assembled from computer tomography (CT) images.

One example use of the invention is treatment of the pancreas. In order to reach a target site in the pancreas, the instrument cord 120 may need to be guided through the mouth, stomach and duodenum. The electrosurgical instrument is arranged to access the pancreas by passing through the wall of the duodenum.

Another example use of the invention is treatment of the lung. In order to reach a target site in the lung, the instrument cord 120 may need to be guided through a patient's airway (via nose or mouth) into the bronchial tree. The electrosurgical instrument may be deployed from a distal end of the instrument cord 120 to treat tissue within the bronchial tree structure.

FIG. 2 is a view down the axis of the instrument cord 120. In this embodiment there are four lumens within the instrument cord 120. The largest lumen is the instrument channel 132 in which the flexible shaft 112 is received. The other lumens comprise an ultrasound signal channel 134, an illumination channel 136, and a camera channel 138 but the invention is not limited to this configuration. For example, there may be other lumens, e.g. for control wires or fluid delivery or suction. Alternatively, the instrument cord 120 may be a simple flexible catheter that defines a single lumen for the flexible shaft.

Figures 3, 4:
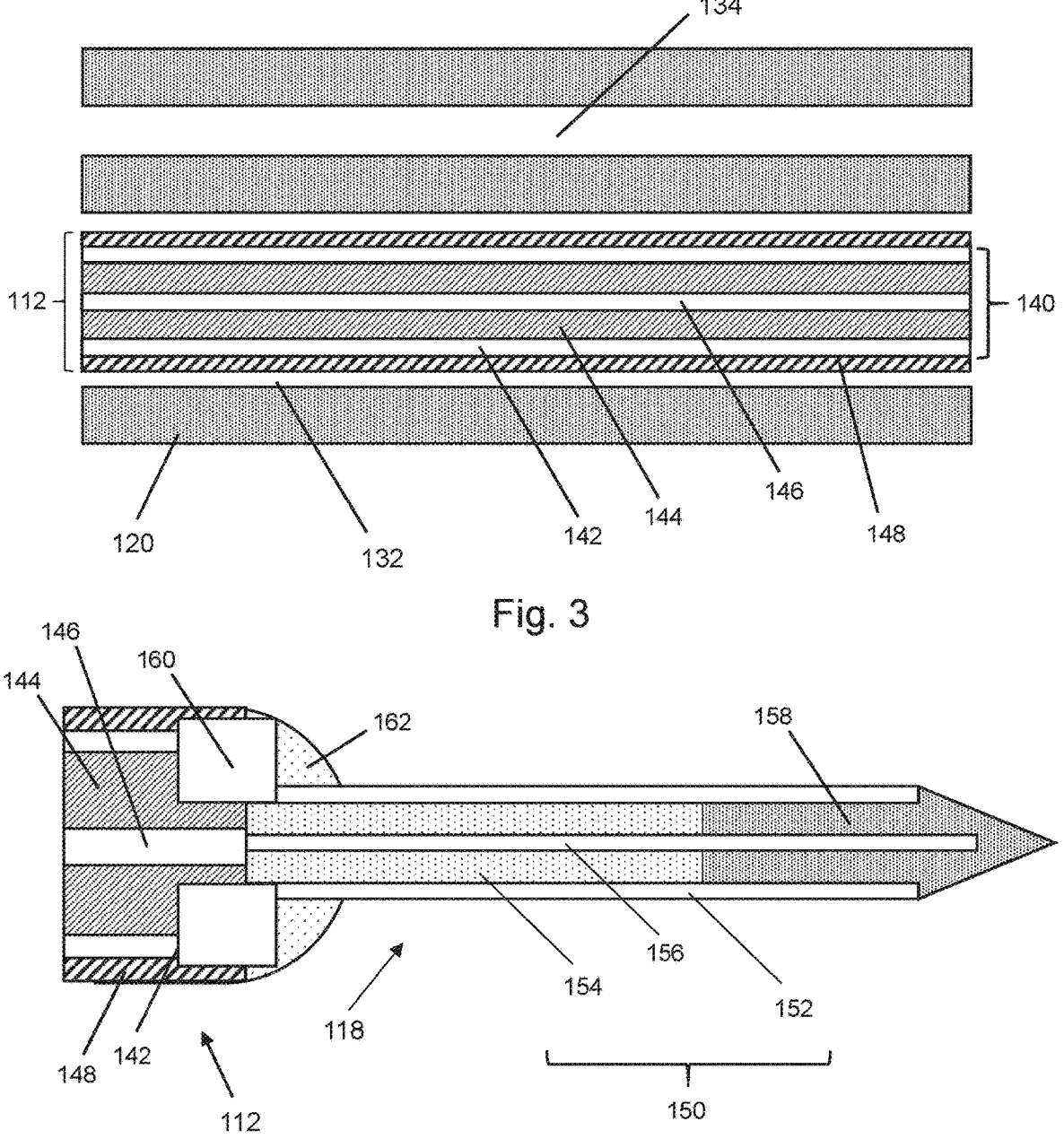
FIG. 3 is a schematic cross-sectional side view of the instrument cord of FIG. 2 with a flexible shaft of an electrosurgical instrument that is an embodiment of the invention passing through the instrument channel thereof.
FIG. 4 is a schematic cross-sectional side view of a distal assembly of an electrosurgical instrument that is an embodiment of the invention.

FIG. 3 is a schematic cross-sectional side view of the instrument cord 120. The instrument channel 132 has the flexible shaft 112 passing therethrough. The flexible shaft 112 comprises a coaxial transmission line 140 formed from a longitudinally extending inner conductor 146 that is surrounded by and separated from an outer conductor 142 by a dielectric material 144. The coaxial transmission line 140 may be a commercially available coaxial cable, e.g. available under the Sucoform brand from Huber+Suhner. The outer conductor may have an outer diameter equal to or less than 2.0 mm. e.g. any of 1.19 mm (0.047"), 1.35 mm (0.053"), 1.40 mm (0.055"), 1.60 mm (0.063"), and 1.78 mm (0.070").

The flexible shaft 112 also includes a flexible elongate thermal transfer element 148, which in this example is a thermally conducting sleeve mounted over the outer conductor 142. The sleeve may be made from a braided metal, such as copper or silver, in order to maintain flexibility.

As discussed above, a proximal end of the thermal transfer element 148 is in thermal communication with the cooling device 130. The thermal transfer element 148 is configured to provide a thermal gradient along the length of the flexible shaft 112 that draw heat away from the distal assembly 118 preferentially in a direction along the shaft.

The cooling device 130 may operate to force cool the proximal end of the thermal transfer element 148 to temperatures lower than 0° C., e.g. less than −50° C., such as −100° C. The thermal transfer element 148 may then act both to cool the coaxial transmission line 140 along its length as well as providing a thermal gradient to draw heat away from the distal assembly 118.

In one example, a thermal isolating layer (not shown) may be provided between the outer conductor and the thermal transfer element 148. This may restrict the transfer of thermal energy from the coaxial transmission line 140 into the thermal transfer element 148, in order to optimise or maximise the thermal gradient along the length of the flexible shaft 112. In other words, the provision of this layer enhances the cooling effect available at the distal assembly 118. The thermal isolating layer may be made from PTFE or other suitable flexible insulator.

FIG. 4 is a schematic cross-sectional side view of the distal assembly 118 (i.e. radiating tip portion) of an electrosurgical instrument that is an embodiment of the invention. The distal end assembly 118 is located at the distal end of the flexible shaft 112. The distal end assembly 118 comprises an elongate rigid probe having an outer diameter that is less than the outer diameter of the coaxial transmission line 140. The elongate rigid probe include a distal coaxial transmission line 150 formed from an inner conductor 156 that is separated from an outer conductor 152 by a dielectric material 154. The inner conductor 156 is electrically connected to the inner conductor 146 of the coaxial transmission line 140 in the flexible shaft 112. In this example, the inner conductor 156 in the distal coaxial transmission line 150 has a smaller outer diameter than the inner conductor 146 of the coaxial transmission line 140 in the flexible shaft 112.

The dielectric material 154 of the distal coaxial transmission line 150 may be the same as or different from the dielectric material 144 of the coaxial transmission line 140 in the flexible shaft 112. In one example, the dielectric material 154 has a greater rigidity than that of the dielectric material 144, in order to facilitate insertion of the elongate probe into tissue.

The elongate probe may further comprise a distalmost tip element 158, e.g. formed from a rigid dielectric (electrically insulating) material. The tip element 158 may have a pointed end as shown in FIG. 4, in order to penetrate tissue. In other example, the end may be rounded, e.g. in a hemispherical manner.

The inner conductor 156 extends into the tip element 158 beyond a distal end of the outer conductor 152 and dielectric material 154 in order to form an antenna for radiating microwave energy received from the coaxial transmission line 140 in the flexible shaft 112. The outer conductor 152 may extend over a portion of the outer surface of the tip element 158. This can assist in securing the tip element 158 to the distal assembly 118, and in ensuring that the field emitted by the antenna has an approximately spherical shape around the distal tip.

The length of the distal coaxial transmission line 150 may be selected to ensure efficient transfer of microwave energy from the coaxial transmission line 140 in the flexible shaft 112 to the antenna. In one example, the distal coaxial transmission line 150 may be configured as a half-wave transformer.

In embodiments of the invention, an interface between the flexible shaft 112 and the distal assembly 118 is configured to draw thermal energy away from the elongate probe, and in particular away from the distal coaxial transmission line 150. There are two aspects to the solution shown in FIG. 4.

The first aspect is provision of a heat sink at a distal end of the elongate probe. In this example, the heat sink is a ring 160 formed from a material having a higher thermal conductivity than the surrounding biological tissue. The material may be copper or silver, for example. The ring 160 is in direct physical contact with the outer conductor 152 of the distal coaxial transmission line 150. The heat sink may operate as an absorbing thermal mass. In other words, the thermal mass of the ring 160 (i.e. ability of the ring to absorb thermal energy) is greater than the thermal mass of the elongate probe (especially the distal coaxial transmission line 150). Accordingly, to achieve thermal equilibrium, heat generated in the coaxial transmission line 150 tends to flow back into the ring 160. The heat sink need not be in the form of a ring. For example, it may be a conductive layer formed over a distal section of the flexible shaft 112 or coaxial transmission line 140. In one example, the coaxial transmission line 140, or a distal portion thereof, may be formed from a tin-coated copper Sucoform 86 cable.

The second aspect is provided by the thermal transfer element 148. In this example, the thermal transfer element 148 is in physical contact with an outer surface of the ring 160. The effect of this is that thermal energy is drawn from the ring 160 by the thermal transfer element 148, which thereby enhances the thermal energy absorption capability of this component.

The first aspect may be implemented alone, i.e. the thermal transfer away from the elongate probe can be provided by the distal heat sink. In this example, no separate cooling device is needed. However, the cooling effect of the ring 160 can be enhanced by the provision of the cooling device and thermal transfer element 148.

In order to prevent cooling effect from the thermal transfer element 148 or ring 160 from affecting biological tissue that may be present at the distal end of the flexible shaft 112, a thermal isolator cap 162 may be provided over the interface between the flexible shaft 112 and distal assembly 118. The cap 162 may be made from epoxy resin or other material with a much lower thermal conductivity than the ring 160.

The thermal isolator cap 162 may also prevent the cooling effect of the ring 160 and thermal transfer element 148 from affecting the shape of the field emitted by the antenna.

Figures 5, 6:
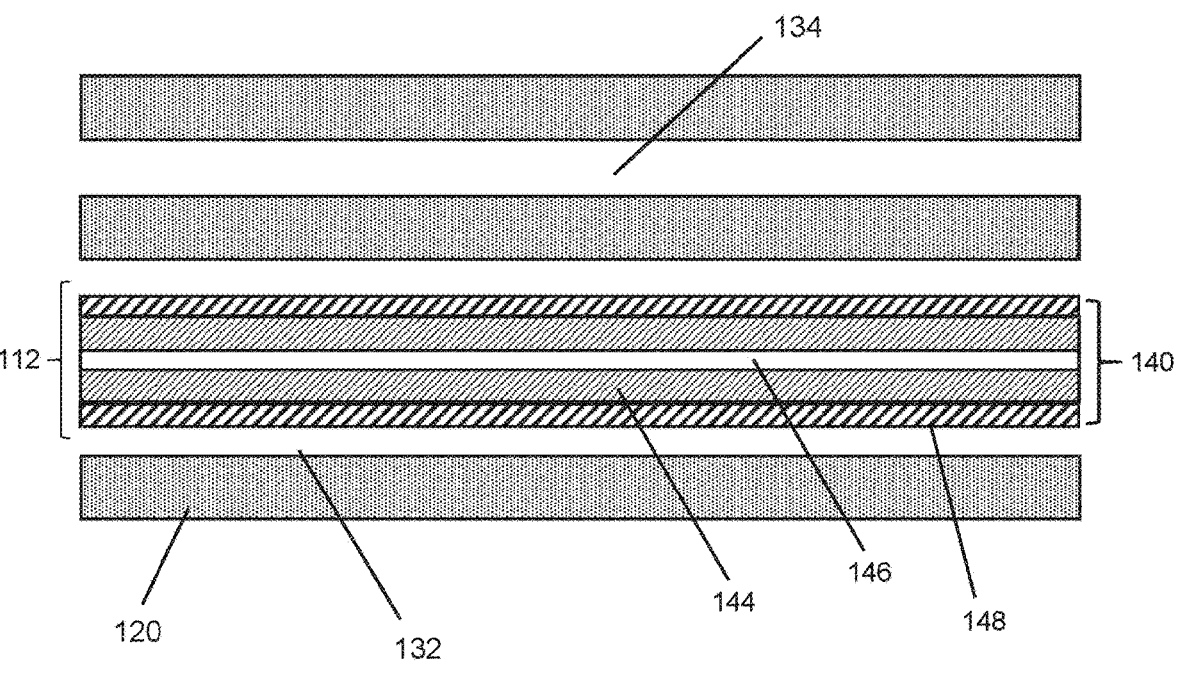
FIG. 5 is a schematic cross-sectional side view of the instrument cord of FIG. 2 with a flexible shaft of an electrosurgical instrument that is another embodiment of the invention passing through the instrument channel thereof.
FIG. 6 is a schematic cross-sectional side view of a handpiece of an electrosurgical system that is an embodiment of the invention.

FIG. 5 is a schematic cross-sectional side view of the instrument cord of FIG. 2 with a flexible shaft 112 of an electrosurgical instrument that is another embodiment of the invention passing through the instrument channel thereof. In this embodiment the thermal transfer element 148 is formed from a conductive material that also acts as the outer conductor of the coaxial transmission line 140. The thermal transfer away from the distal assembly in this example is achieved by force cooling a distal end of the outer conductor of the coaxial transmission line. In additional examples, the cooling effect may be enhanced further by force cooling the inner conductor 146.

FIG. 6 is a schematic cross-sectional side view of a handpiece 180 of an electrosurgical system that is an embodiment of the invention. The handpiece 180 may perform the function of the interface joint 106 discussed above, in that it combines into a single flexible shaft 112 inputs from a cooling device 130, an electrosurgical generator (via interface cable 104) and a control mechanism 109.

The control mechanism 109 comprises a slider 182 that is movable back and forth relative to a housing 184 of the handpiece 180. The slider 182 is connected to a conductive bar 170 that moves within the housing 184 within first signal transfer element 168. In this example, the first signal transfer element 168 is a conductive sleeve within which the bar 170 slides. The bar 170 is in electrical contact with the sleeve, which in turn is connected to an inner conductor of the interface cable 104 via connector 166. The conductive bar 170 is connected at its distal end to the proximal end of the coaxial transmission line 140. The conductive bar 170 is electrically connected to the inner conductor 146 of the coaxial transmission line 140. A proximal end of the coaxial transmission line 140 is slidably received in a second signal transfer element 172, which is in electrical contact with a proximal portion 174 of the outer conductor of the coaxial transmission line 140. The second signal transfer element 172 is electrically connected to an outer conductor of the interface cable 104 via connector 166.

By the above mechanism, the coaxial transmission line 140 is longitudinally slidable by the control mechanism 109, whilst also receiving microwave power from the interface cable 104.

In this example, the thermal transfer element 148 is a sleeve formed over and fixed or otherwise secured to the coaxial transmission line 140. The proximal portion 174 of the outer conductor of the coaxial transmission line 140 extends in a proximal direction beyond a proximal end of the thermal transfer element 148 in order to be received by the second signal transfer element 172. Meanwhile, a proximal portion of the thermal transfer element 148 is slidably received in a cooling jacket 164, which in this is an annular cooling element in thermal communication with the cooling device 130. The cooling device 130 operates to draw heat from the cooling jacket 164, which in turn draws heat from and therefore cools the thermal transfer element 148.

The invention claimed is:

1. An electrosurgical instrument comprising:
a flexible coaxial transmission line arranged to convey microwave energy;
a radiating tip portion connected at a distal end of the flexible coaxial transmission line and configured to receive the microwave energy, the radiating tip portion comprising:
  a distal coaxial transmission line for conveying the microwave energy; and
  a needle tip mounted at a distal end of the distal coaxial transmission line, the needle tip being arranged to deliver the microwave energy into biological tissue; and
a heat sink mounted at an interface between the flexible coaxial transmission line and radiating tip portion, and
a thermal isolator cap mounted over the interface between the flexible coaxial transmission line and radiating tip portion to thermally isolate the heat sink from surrounding biological tissue;
wherein the heat sink is in thermal communication with a proximal end of the distal coaxial transmission line and configured to draw thermal energy from the radiating tip portion,
wherein a thermal mass of the heat sink is greater than a thermal mass of the radiating tip portion, and
wherein a maximum outer diameter of the radiating tip portion is smaller than an outer diameter of the flexible coaxial transmission line.

2. The electrosurgical instrument of claim 1, wherein the heat sink is a solid body.

3. The electrosurgical instrument of claim 2, wherein the solid body is disposed between an outer conductor of the distal coaxial transmission line and an outer conductor of the flexible coaxial transmission line.

4. The electrosurgical instrument of claim 1, wherein the heat sink is an annular body mounted around the proximal end of the distal coaxial transmission line.

5. The electrosurgical instrument of claim 1, wherein the thermal isolator cap is formed from epoxy.

6. The electrosurgical instrument of claim 1, wherein the radiating tip portion has a maximum outer diameter that is 1.0 mm or less.

7. The electrosurgical instrument of claim 1, wherein the distal coaxial transmission line is a half wavelength transformer.

8. The electrosurgical instrument of any preceding claim further comprising a thermal transfer element disposed along the flexible coaxial transmission line, wherein the thermal transfer element provides a thermal gradient that draws heat energy from the radiating tip portion.

9. The electrosurgical instrument of claim 8, wherein the thermal transfer element is a sleeve of thermally conductive material mounted around an outer conductor of the flexible coaxial transmission line.

10. The electrosurgical instrument of claim 9, wherein the sleeve is made from braided metal.

11. The electrosurgical instrument of claim 8, wherein the thermal transfer element is an outer conductor of the flexible coaxial transmission line.

12. The electrosurgical instrument of claim 8, wherein a distal portion of the thermal transfer element is in thermal communication with the heat sink to draw thermal energy in a proximal direction along the flexible coaxial transmission line.

13. The electrosurgical instrument of claim 8, wherein the thermal transfer element comprises a solid body.

14. An electrosurgical system comprising:
an electrosurgical generator configured to generate microwave energy for ablating biological tissue;
an electrosurgical instrument according to claim 9 connected to receive the microwave energy from the electrosurgical generator; and
a cooling device arranged to force cool a proximal portion of the thermal transfer element and the electrosurgical instrument.

15. The electrosurgical system of claim 14, wherein the cooling device is a thermoelectric cooler.

16. The electrosurgical system of claim 14 further including a surgical scoping device having a flexible insertion cord for insertion into a patient's body, the flexible insertion cord having an instrument channel running along its length, and wherein the electrosurgical instrument is dimensioned to be received within the instrument channel.

17. The electrosurgical system of claim 16 further comprising a handpiece having a housing for receiving a proximal end of the electrosurgical instrument, wherein the handpiece comprises a control mechanism arranged to move the electrosurgical instrument relative to the housing to deploy a distal end of the electrosurgical instrument at a distal end of the instrument channel.

18. An electrosurgical system comprising:
an electrosurgical instrument comprising:
  a flexible coaxial transmission line arranged to convey microwave energy;
  a radiating tip portion connected at a distal end of the flexible coaxial transmission line and configured to receive the microwave energy, the radiating tip portion comprising:
    a distal coaxial transmission line for conveying the microwave energy; and
    a needle tip mounted at a distal end of the distal coaxial transmission line, the needle tip being arranged to deliver the microwave energy into biological tissue;
  a heat sink mounted at an interface between the flexible coaxial transmission line and radiating tip portion; and
  a thermal transfer element disposed along the flexible coaxial transmission line, wherein the thermal transfer element provides a thermal gradient that draws heat energy from the radiating tip portion;
  wherein the heat sink is in thermal communication with a proximal end of the distal coaxial transmission line and configured to draw thermal energy from the radiating tip portion, and
  wherein a maximum outer diameter of the radiating tip portion is smaller than an outer diameter of the flexible coaxial transmission line; and
a cooling device arranged to force cool a proximal portion of the thermal transfer element and the electrosurgical instrument.

* * * * *